United States Patent
Raemakers-Franken et al.

(10) Patent No.: US 7,491,520 B2
(45) Date of Patent: Feb. 17, 2009

(54) BIOCHEMICAL SYNTHESIS OF 6-AMINO CAPROIC ACID

(75) Inventors: Petronella C. Raemakers-Franken, Budel (NL); Petrus M. M. Nossin, Nederweert (NL); Paul M. Brandts, Limbricht (NL); Marcel G. Wubbolts, Sittard (NL); Wijnand P. H. Peeters, Maasbree (NL); Sandra Ernste, Landgraaf (NL); Stefaan M. A. Wildeman De, Kessel-Lo (BE); Martin Schuermann, Juelich (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/586,132

(22) PCT Filed: Jan. 17, 2005

(86) PCT No.: PCT/EP2005/000555

§ 371 (c)(1),
(2), (4) Date: Nov. 28, 2006

(87) PCT Pub. No.: WO2005/068643

PCT Pub. Date: Jul. 28, 2005

(65) Prior Publication Data

US 2007/0254341 A1    Nov. 1, 2007

(30) Foreign Application Priority Data

Jan. 19, 2004   (EP)   .................. 04075079

(51) Int. Cl.
*C12P 13/00* (2006.01)
*C12P 21/02* (2006.01)
*C12N 9/56* (2006.01)
*C12N 1/20* (2006.01)

(52) U.S. Cl. ...................... 435/128; 435/71.1; 435/189; 435/221; 435/252.7; 435/252.33

(58) Field of Classification Search ........................ None
See application file for complete search history.

(56) References Cited

U.S. PATENT DOCUMENTS 4,080,259 A   3/1978   Boesten et al.

| | | |
|---|---|---|
| 5,599,791 A | 2/1997 | Tavecchia et al. |
| 6,194,572 B1 | 2/2001 | Buijs et al. |
| 2004/0248274 A1 | 12/2004 | Boesten et al. |
| 2007/0117191 A1 | 5/2007 | Kurihara et al. |

FOREIGN PATENT DOCUMENTS

| | | |
|---|---|---|
| CN | 1358841 | 7/1992 |
| EP | 0494078 | 7/2002 |
| EP | 1473368 | 11/2004 |
| JP | 50-006776 | 1/1975 |
| WO | 03/066863 | 8/2003 |
| WO | 03/106691 | 12/2003 |

OTHER PUBLICATIONS

Miura et al. "Molecular cloning of the *nemA* gene encoding N-ethylmaleimide reductase from *Escherichia coli*" Biol. Pharm. Bull. 20:110-112 (1997).
Rohdich et al. "Enoate reductases of Clostridia: Cloning, sequencing, and expression" J. Biol. Chem. 276:5779-5787 (Feb. 2001).
Simon et al. "Chiral compounds synthesized by biocatalytic reductions" Angew. Chem. Int. Ed. Engl. 24:539-553 (Jul. 1985).
Steinbacher et al. "Enoate reductase family" STN database Accession No. 2003:101473 abstract (Jul. 2002).
Thanos et al. "Electro-enzymic viologen-mediated sterospecific reduction of 2-enoates with free and immobilized enoate reductase on cellulose filters or modified carbon electrodes" J. Biotech 6:13-29 (1987).
Whelan et al. "Nylon 6 (PA6)" Kunststofen Rubber 39:38-39 (1986).
Int'l Search Report for PCT/EP2005/000555 dated Aug. 17, 2005.
Int'l Preliminary Report on Patentability for PCT/EP2005/000555 dated May 4, 2006.

*Primary Examiner*—Tekchand Saidha
*Assistant Examiner*—Md. Younus Meah
(74) *Attorney, Agent, or Firm*—Nixon & Vanderhye P.C.

(57) ABSTRACT

The invention relates to biochemical synthesis of 6-amino caproic acid from 6-aminohex-2-enoic acid compound or from 6-amino-2-hydroxyhexanoic acid, by treatment with an enzyme having α,β-enoate reductase activity towards molecules containing an α,β-enoate group and a primary amino group. The invention also relates to processes for obtaining suitable genetically engineered cells for being used in such biotransformation process, and to precursor fermentation of 6-amino caproic acid from intermediates leading to 6-amino caproic acid. Finally, the invention relates to certain novel biochemically produced compounds, namely 6-aminohex-2-enoic acid, 6-aminohexanoic acid, as well as to caprolactam produced therefrom and to nylon-6 and other derivatives produced from such biochemically produced compounds or caprolactam.

27 Claims, No Drawings

SEQUENCE LISTING

```
<160> NUMBER OF SEQ ID NOS: 8

<210> SEQ ID NO 1
<211> LENGTH: 100
<212> TYPE: DNA
<213> ORGANISM: Artificial Sequence
<220> FEATURE:
<223> OTHER INFORMATION: primer

<400> SEQUENCE: 1
aagaagaccg gatcctacct gacgcttttt atcgcaactc tctactgttt ctccataccc      60 gtttttggg ctaacacaag tttgtacaaa aaagctgaac                            100

<210> SEQ ID NO 2
<211> LENGTH: 37
<212> TYPE: DNA
<213> ORGANISM: Artificial Sequence
<220> FEATURE:
<223> OTHER INFORMATION: primer

<400> SEQUENCE: 2
ttgttctacg taaccacttt gtacaagaaa gctgaac                              37

<210> SEQ ID NO 3
<211> LENGTH: 68
<212> TYPE: DNA
<213> ORGANISM: Artificial Sequence
<220> FEATURE:
<223> OTHER INFORMATION: primer

<400> SEQUENCE: 3
gggacaagtt tgtacaaaaa agcaggctag gaggaattaa ccatgaaaaa caaatcttta      60
tttgaacc                                                              68

<210> SEQ ID NO 4
<211> LENGTH: 56
<212> TYPE: DNA
<213> ORGANISM: Artificial Sequence
<220> FEATURE:
<223> OTHER INFORMATION: primer
```

```
<400> SEQUENCE: 4 gggaccact ttgtacaaga aagctgggtc taacagttaa gtccaatttc atttcc        56

<210> SEQ ID NO 5
<211> LENGTH: 67
<212> TYPE: DNA
<213> ORGANISM: Artificial Sequence
<220> FEATURE:
<223> OTHER INFORMATION: primer

<400> SEQUENCE: 5
gggacaagtt tgtacaaaaa agcaggctag gaggaattaa ccatggtagc ctataccaga   60
cttttttg                                                            67

<210> SEQ ID NO 6
<211> LENGTH: 50
<212> TYPE: DNA
<213> ORGANISM: Artificial Sequence
<220> FEATURE:
<223> OTHER INFORMATION: primer

<400> SEQUENCE: 6 gggaccact ttgtacaaga aagctgggtc taaatccctc gccctacctc               50

<210> SEQ ID NO 7
<211> LENGTH: 69
<212> TYPE: DNA
<213> ORGANISM: Artificial Sequence
<220> FEATURE:
<223> OTHER INFORMATION: primer

<400> SEQUENCE: 7
ggggacaagt ttgtacaaaa aagcaggcta ggaggaatta accatgtcat ctgaaaaact   60
gtattcccc                                                           69

<210> SEQ ID NO 8
<211> LENGTH: 55
<212> TYPE: DNA
<213> ORGANISM: Artificial Sequence
<220> FEATURE:
<223> OTHER INFORMATION: primer

<400> SEQUENCE: 8 gggaccact ttgtacaaga aagctgggtt tacaacgtcg ggtaatcggt atagc         55
```

BIOCHEMICAL SYNTHESIS OF 6-AMINO CAPROIC ACID

This application is the U.S. national phase of international application PCT/EP2005/000555 filed 17 Jan. 2005 which designated the U.S. and claims benefit of EP 04075079.6, dated 19 Jan. 2004, the entire content of which is hereby incorporated by reference.

The present invention relates to a new process for biochemical synthesis of 6-amino caproic acid. 6-Amino caproic acid is hereinafter also referred to as 6-ACA. The compound 6-amino caproic acid (IUPAC name: 6-amino-hexanoic acid) is a possible intermediate for the production of ε-caprolactam (hereinafter more briefly referred to as caprolactam), which is the basis for nylon-6 production. On the other hand, 6-amino caproic acid also may be formed by hydrolysis of caprolactam. Caprolactam is a bulk chemical and is being produced at very large scale throughout the world.

Basic chemicals for the industrial production of caprolactam generally are bulk chemicals such as benzene, cyclohexane, cyclohexanone, etc. from which cyclohexanone oxime is being produced, that is then converted into caprolactam via a so-called Beckmann rearrangement. However, in the recycling of nylon-6 carpet waste materials, for instance, 6-amino caproic acid (as well as some other products formed in the depolymerization step of nylon-6) may be used for the synthesis of caprolactam by a cyclization reaction. In the industrial recycling of nylon-6 the production of caprolactam is often the last synthesis step. 6-Amino caproic acid (6-ACA) is thus suitable for the synthesis of caprolactam, and subsequently for the production of nylon-6. 6-ACA, however, also can be used directly as raw material for the production of nylon-6.

For the cyclization of 6-ACA and/or esters thereof, various processes are known to the skilled man. For instance, reference can be made to the processes as are being described in U.S. Pat. No. 6,194,572 wherein 6-ACA and/or esters thereof are treated in a reaction zone, in the absence of a catalyst, with superheated steam at a temperature in the range of from 270 to 400° C. and a pressure in the range of from 0.5 to 2 MPa. These processes can be operated continuously and the caprolactam formed can be isolated by partial condensation at a temperature in the range of from 100 to 170° C. immediately after the reaction mixture leaves the reaction zone. Direct conversion of 6-ACA into nylon-6, for instance can be done as described in JP-4050232-A.

As meant in the present patent application, the term "biochemical synthesis" (a term that, in the context of this patent application, alternatively is referred to as "biotransformation") includes not only processes which involve—besides a number of purely chemical reaction steps—one or more biocatalytic reactions, but also purely biochemical processes using whole cells of suitable production strains. Such purely biochemical processes, respectively, are referred to as fermentations in case the biochemical synthesis starts from a suitable carbon source, or are referred to as precursor fermentations in case the biosynthesis starts from an intermediate product already having a carbon skeleton from which the target molecule to be synthesized can be obtained. The processes may be carried out either under aerobic or under anaerobic conditions.

Biochemical synthesis can be carried out either in vivo or in vitro. Generally, in vivo processes are processes carried out when using living cells (the term "living cells" thereby also including so-called resting cells); in vitro processes, on the other hand, usually are being carried out using cell lysates or (partly) purified enzymes. The biochemical synthesis as meant herein, however, also may be carried out using permeabilized cells; the differentiation between in vivo and in vitro, however, does not make much sense for processes being carried out with permeabilized cells.

The present invention also relates to processes for obtaining suitable genetically engineered host cells for being used in a biotransformation process for the synthesis of 6-amino caproic acid, and also specifically to hitherto unknown processes for precursor fermentation of 6-amino caproic acid from intermediates leading to 6-amino caproic acid namely from 6-aminohex-2-enoic acid, or from a compound capable of being converted thereto one, namely 6-amino-2-hydroxy-hexa-noic acid. The said compounds 6-aminohex-2-enoic acid and 6-amino-2-hydroxy-hexanoic acid (as will be explained hereinafter) are being referred to, respectively, as 6-AHEA and 6-AHHA in the context of the present application. In precursor fermentation of 6-amino caproic acid suitable intermediates, as described below, are being made available for the precursor fermentation in such way that they are present therein at a non-limiting and non-inhibiting concentration, for instance by feeding into the reaction vessel wherein the biochemical synthesis (i.e. conversion) is being carried out.

The present invention further also specifically relates to novel host cells having enoate reductase activity towards 6-aminohex-2-enoic acid, i.e. towards 6-AHEA. Especially it also relates to novel host cells having aerostable enoate reductase activity towards 6-AHEA. As used herein, the term "aerostable" means oxygen-tolerant.

Finally, as also will be explained hereinafter, the present invention relates to the novel biochemically produced compounds 6-AHEA and 6-ACA, as well as to caprolactam produced from such 6-ACA, and to nylon-6 or other derivatives produced from such biochemically produced compounds or such caprolactam.

In general, the routes to 6-ACA as are known until today are quite laborious and troublesome. Usually, if 6-ACA is not being produced from waste nylon-6 materials, these known routes require relatively expensive starting materials and reactants (e.g. butadiene and hydrogen gas), and relatively severe reaction conditions of temperature and pressure in a multi-step and multi-reactor design, as well as the use of expensive catalyst systems. Accordingly, there remains a need for alternative routes to 6-ACA, preferably from much less expensive raw materials. It is well known that naturally growing, and thus renewable, materials from agricultural production are the basis for carbon sources such as glucose (or other appropriate carbon sources and mixtures thereof) that can be used in fermentation or precursor fermentation. Such renewable materials are relatively cheap and abundantly available. In general, it is considered to be very advantageous if renewable materials can be used as starting materials for all kinds of chemical materials.

It is an aim of the present invention to enable the—so far unknown—production of 6-ACA by biochemical synthesis (i.e. by biotransformation).

The present inventors surprisingly have found a novel process for the biochemical synthesis of 6-amino caproic acid wherein either 6-aminohex-2-enoic acid of formula [1] (6-AHEA)

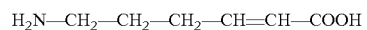  [1]

or wherein 6-amino-2-hydroxyhexanoic acid (6-AHHA), a compound capable of being transformed into 6-aminohex-2-enoic acid, is treated with an enzyme having α,β-enoate reductase activity towards molecules containing an α,β- enoate group and a primary amino group, in particular with an enzyme having α,β-enoate reductase activity towards 6-aminohex-2-enoic acid.

As meant herein, enzymes having α,β-enoate reductase activity towards molecules containing an α,β-enoate group and a primary amino group are understood to be enzymes that are capable of converting the α,β-carbon-carbon double bond at the α,β-position next to a carboxylic acid (—COOH) (or carboxylate (—COO⁻), or ester (—COOR, with R representing a lower alkyl group of at most 6 C-atoms)) group into a carbon-carbon single bond in molecules also containing a primary amino group, i.e. an —NH$_2$ group not forming part of an amide group. Mono- or disubstituted amino groups are not comprised in the definition of primary amino groups as used herein. The term α,β-enoate reductase activity is meant to include such activity at all possible levels of measurable activity, including increased levels of activity as can be achieved by methods known to the skilled man, such as by overexpression, induction or otherwise regulating of the relevant gene, increasing the copy number of the relevant gene, increasing the endogenous activity of the relevant enzyme, etc., or by optimizing the assay conditions.

In addition to 6-AHEA, also the corresponding saturated, α-hydroxy-substituted compound 6-AHHA, capable of being transformed into 6-AHEA by dehydratation may be applied in the process of the present invention. Within the context of this patent application this compound is considered to be equivalent to the α-unsubstituted α,β-enoate 6-AHEA.

It is to be noticed, that the biochemical reaction as has been found by the present inventors, has not yet been described nor suggested in the prior art for the conversion of molecules containing an α,β-enoate group and a pimary amino group, even though enzymes having α,β-enoate reductase activity, most often specifically for α,β-enoates containing an a-substituent not being equal to hydrogen, already were known to the skilled man for other types of reactions for a broad range of substrates. Generally such known reactions of enzymes with α,β-enoate reductase activity were aimed at creating enantiospecific enzymatic syntheses. For instance see H. Simon et al. in Angew. Chem. Int. Ed. Engl., Vol. 13 (1974), p. 608-609; B. Rambeck et al., ibid. at page 609; I. Thanos et al. in J. Biotechnol. 9, 13-29 (1987); H. Simon et al. in Angew. Chem. Int. Ed. Engl., Vol. 24 (1985), p. 539-553; and U.S. Pat. No. 4,464,235. A survey dealing with enzymes having α,β-enoate reductase activity can be found in Chem. Biochem. Flavoenzymes (1991), Chapter 11, pages 317-328 by H. Simon; publisher: CRC, Boca Raton. The latter of these references suggests, that the enoate reductase activity will involve a hydride-transfer from the reduced enzyme to the enoate compound. I. Thanos et al. (cited above) focused on the electroenzymatic reduction aspects when using enoate reductase from *Clostridium tyrobutyricum* DSM1460 for α-substituted enoates. Other examples of enzymes having α,β-enoate reductase activity are being shown for the synthesis of stereochemically pure α-substituted carbonyl compounds in WO-03/066863. This reference does not show any primary amino group-containing substrate for the enoate reductases used. There is, thus, no indication at all, that enzymes with α,β-enoate reductase activity can suitably be used for the biochemical synthesis of compounds that are unsubstituted at the α-position next to a carboxylic group and that also contain a primary amino group, for instance, 6-ACA. In fact, the skilled man, taking into account the abovementioned presumable hydride-transfer mechanism, would rather expect that the presence of a primary amino group in a molecule to be converted by means of an enzyme having α,β-enoate reductase activity would have negative effect on such reaction. The expectedly positively charged amino group would seem to be the preferred acceptor for the hydride to be transferred, thereby negatively interfering with the enoate reductase activity.

It is further to be noticed, that the remark made by Steinbacher et al. (see STN Database accession no. 2003:101473) that enoate reductases have broad substrate specificity, a remark that is also consistent with the data from other references, e.g. of H. Simon et al. cited above, where the use of a broad range of substrates for the enoate reductase reaction in the strain *Clostridium tyrobutyricum* DSM1460 (the same strain as also had been used in the work of I. Thanos et al., cited above) is being shown, does not change said view.

Moreover, in literature, cloning, sequencing and expression of enoate reductases from different clostridia has been described (see F. Rohdich, et al. in J. Biol. Chem. 276(6), 5779-5787 (2001). Especially, the enoate reductase (enr) genes of *Clostridium tyrobutyricum* DSM1460 and *Clostridium thermoaceticum* DSM1974 (a strain quite recently also having been renamed together with a number of *Clostridium* species, and thus now also is being referred to, as *Moorella thermoacetica*) were cloned and sequenced.

However, such cloning so far never has been carried out in any species from either of, for instance, the genera *Bacillus, Corynebacterium,* or *Pichia*. In particular, however, as to the cloning of the enr-gene from *Moorella thermoacetica* and from *Clostridium tyrobutyricum* in *E. coli* as has been described by F. Rohdich. As to these clonings it is to be noticed, that the latter (from *C. tyrobutyricum*) has not been tested by Rohdich et al. under anaerobic conditions (i.e. with growth under anaerobic conditions), and—in tests under aerobic conditions—resulted in an inactive form of the enoate reductase, whereas the former (from *M. thermoacetica*) gave the same result when expressed aerobically, and only yielded an active form of the enoate reductase under anaerobic conditions. Moreover, in WO-03/066863 cloning in *E. coli* of enoate reductase enzymes obtained from *Burkholderia* species is being described, and these enzymes have been sequenced.

Accordingly, none of the cited references teaches the 6-ACA forming reaction as forms the basis of the present invention.

As the inventors have found, the enzyme having α,β-enoate reductase activity (as used in the process of the present invention) can be any suitable enzyme (i.e. the enzyme is suitable if it can be confirmed to have α,β-enoate reductase activity towards towards molecules containing an α,β-enoate group and a primary amino group, especially towards 6-aminohex-2-enoic acid) originating from a large group of genera of microorganisms (anaerobic ones as well as aerobic ones), such as, for instance, of *Acetobacterium, Achromobacter, Acremonium, Agrobacterium, Alcaligenes, Bacillus, Bradyrhizobium, Burkholderia, Caloramator, Cephalosporium, Clostridium, Escherichia, Eubacterium, Filifactor, Fusobacterium, Kluyveromyces, Mesorhizobium, Moorella, Ochrobactrum, Oxalophagus, Oxobacter, Paenibacillus, Pseudomonas, Ralstonia, Rhizobium, Rhodotorula, Salmonella, Shigella, Sinorhizobium, Sporohalobacter, Syntrophospora, Thermoanaerobacter, Thermoanaerobacterium, Tilachlidium, Vibrio, Xanthobacter,* or *Yersinia*.

Preferably in the process of the present invention, the enzyme having α,β-enoate reductase activity is an enzyme originating from a microorganism from the group of species of *Acetobacterium* sp., *Acremonium* sp., *Agrobacterium* sp., *Burkholderia* sp., *Cephalosporium* sp., *Clostridium* sp.,

*Escherichia* sp., *Moorella* sp., *Ochrobactrum* sp., *Pseudomonas* sp., *Salmonella* sp., *Shigella* sp., *Tilachlidium* sp., *Yersinia* sp., and *Vibrio* sp.

More preferably, the enzymes having α,β-enoate reductase activity are enzymes originating from *Acremonium* sp., *Clostridium* sp., *Moorella* sp. or *Ochrobactrum* sp.

Most preferably, the enzyme having α,β-enoate reductase activity is an enzyme from *Acremonium strictum* CBS114157 (deposit date Dec. 19, 2003; deposited under the terms of the Budapest treaty), *Clostridium tyrobutyricum* DSM1460 (available from the Deutsche Sammlung Mikroorganismen und Zellkulturen), *Moorella thermoacetica* DSM1974 (available from the Deutsche Sammlung Mikroorganismen und Zellkulturen) (an enzyme which—also under DSM1974—until Jan. 1, 1980, was named *Clostridium thermoaceticum*), *Ochrobactrum anthropi* NCIMB41200 (deposit date Dec. 16, 2003; deposited under the terms of the Budapest treaty), or *Clostridium kluyveri* DSM555 (available from the Deutsche Sammlung Mikroorganismen und Zellkulturen). In this context it is to be noticed that a number of *Clostridium* species quite recently have been renamed. The names given hereinabove are thus meant to be indicative of the variety of species and strains (cells) that can be considered for obtaining therefrom enzymes with α,β-enoate reductase activity.

Good results in the biochemical conversion to 6-ACA according to the present invention have been achieved by the inventors when using an enzyme having α,β-enoate reductase activity from *Clostridium tyrobutyricum* DSM1460, or from *Moorella thermoacetica* DSM1974.

Preferably the enzyme having α,β-enoate reductase activity towards molecules containing an α,β-enoate group and a primary amino group has aerostable α,β-enoate reductase activity. This means, that the enzyme, without any significant deactivation, i.e. the deactivation will be not more than the standard deviation of enzyme activity during the biotransformation process, will be able to catalyze the desired biotransformation under conditions where free oxygen is present. Such enzymes having aerostable activity also may be called oxygen-tolerant enzymes.

Accordingly, in a preferred embodiment of the present invention, the enzyme having α,β-enoate reductase activity has aerostable α,β-enoate reductase activity and is an enzyme originating from a microorganism from the group of species of *Agrobacterium* sp., *Burkholderia* sp., *Escherichia* sp., *Pseudomonas* sp., *Salmonella* sp., *Shigella* sp., *Yersinia* sp., and *Vibrio* sp. More preferably, the enzyme having aerostable α,β-enoate reductase activity is an enzyme originating from an *Escherichia coli* species, and most preferably the enzyme originates from *Escherichia coli* K12.

The process of the present invention very suitably can be carried out by conversion of 6-aminohex-2-enoic acid into 6-amino caproic acid at a pH in the range of from 3 to 9, preferably of from 4 to 8, more preferably of from 5 to 8, and most preferably of from 5.5 to 7 under anaerobic conditions and of from 6.5 to 8 under aerobic conditions.

The starting material 6-aminohex-2-enoic acid (6-AHEA) can be made available for the biochemical conversion according to the present invention by providing this compound, or a product capable of being metabolized thereto (but being different from a mere carbon source, such as for instance glucose), in such way that it is present in the reactor used at a non-limiting and non-inhibiting concentration, for instance by feeding into the reaction vessel, e.g. a fermentor, where the biochemical process is being carried out. Processes according to the invention in which the 6-AHEA (or a metabolisable precursor thereof) is used in such way in the reaction vessel, can also be referred to as "precursor fermentations".

Of course, as meant herein, 6-AHEA (or any product capable of being metabolized thereto, and being different from a mere carbon source) also can be made available for the conversion according to the present invention by any suitable biochemical process occurring in the microorganism containing the α,β-enoate reductase activity. It is known, for instance, that lysine can be produced by biotransformation in *Corynebacterium glutamicum* cells (for instance, see Pfefferle W., in Adv. Biochem. Eng. (2003), Vol. 79, p. 59-112). The fact that the complete genome sequence of *Corynebacterium glutamicum* now has become available has had major impact on the improvement of the biotechnological manufacture of lysine. Assuming that lysine in the microorganism then subsequently can be converted into 6-AHEA, a process that hitherto has not been disclosed nor suggested, this can be a suitable method for making 6-AHEA available for the conversion of the present invention.

Lysine produced by biochemical synthesis (biotransformation) can be converted into 6-AHEA by chemical methods readily available to the skilled man. For instance, by first protecting the ε-amino group using the lysine-copper(II) complex method as described in Houben-Weyl, Methods of Organic Chemistry (4th edition), Vol E22a, Thieme, Stuttgart, 2002, page 166-191. Optional protecting groups are acetyl, benzoyl, phenylacetyl, benzyloxycarbonyl or phthaloylimide. Subsequent nitrosation reaction of the α-amino-group in the presence of mercaptans or selenols then results in the formation of the corresponding α-thio or α-seleno ether. This nitrosation can be performed either in aqueous medium with $NaNO_2/H_2SO_4$ or under anhydrous conditions using, for example, iso-amylnitrite. Suitable examples of mercaptans are (substituted) thiophenol and benzylmercaptan; benzeneselenol is preferred as selenol in this reaction. Subsequent oxidation of the α-thio ether or α-seleno ether with $H_2O_2$ followed by an in situ elimination reaction will result in ε-protected 6-AHEA. An example of this procedure is described by S. Bory, M. Gaudry, A. Marquet; Nouveau Journal de Chimie (1986), 10, 709-713. By acid or base catalysed hydrolysis of the ε-protecting group 6-AHEA is obtained.

In such case where 6-AHEA is being produced biochemically in the cell (or from lysine that has been produced by biotransformation), the resulting 6-ACA (and the caprolactam derived therefrom after excretion from the cell and cyclization by any known methods) will be easily distinguishable from 6-ACA (and/or caprolactam obtained therefrom, respectively products derived therefrom, for instance nylon-6 obtained from such caprolactam) as is being obtained by chemical routes from fossil feedstock. In the latter case absence of $^{14}C$ in the carbon chains of the molecules will be easily demonstrable. Alternatively, the $^{12}C$ versus $^{13}C$ versus $^{14}C$ isotope ratio (as can be determined by Stable Isotope Ratio Mass Spectrometry (SIRMS) methods, or by so-called Site-Specific Natural Isotopic Fractionation studied by Nuclear Magnetic Resonance (SNIF-NMR® as are being used for identification of biosubstances) may be used as a fingerprint for the origin of the 6-ACA (and/or caprolactam) because the $^{12}C$ versus $^{13}C$ versus $^{14}C$ isotope ratio will have about the same value as is occurring in environmental carbon dioxide.

The starting material, 6-aminohex-2-enoic acid (6-AHEA), also can be obtained purely chemically, for instance, analogous to steps a and i from scheme 2 in the method described by P. Hughes et al. for the synthesis of threo-3-hydroxylysine in J. Org. Chem. vol. 59 (1994), pages 5799-5802. This is being shown in the experimental part of this application.

The process according to the invention is preferably carried out in a host organism selected from the group of genera consisting of *Aspergillus, Bacillus, Corynebacterium, Escherichia,* and *Pichia*. Host organisms belonging to the group of *Corynebacterium* sp., for instance, *C. glutamicum*, are especially preferred because these microorganisms are known to be suitable for biosynthetic production of lysine.

In a particularly preferred embodiment of the present invention, the host strain and, thus, host cell suitable for the biochemical synthesis of 6-amino caproic acid is selected from the group of *Escherichia coli, Bacillus, Corynebacterium glutamicum, Aspergillus niger* or *Pichia pastoris* host cells, in which an α,β-enoate reductase gene encoding an enzyme having α,β-enoate reductase activity towards molecules containing an α,β-enoate group and a primary amino group is cloned and expressed. Instead of any of such said α,β-enoate reductase gene also any other gene coding for an enzyme having α,β-enoate reductase activity and capable of converting 6-AHEA into 6-ACA at an adequate degree, may be used and is deemed to be encompassed in the scope of this claimed embodiment. From the cells mentioned in the present application only *Escherichia coli* cells cloned with either the α,β-enoate reductase gene from *Moorella thermoacetica* DSM1974, or from *Clostridium tyrobutyricum*, have been described in the prior art; the other cells mentioned are novel cells.

Moreover, as the present inventors have found, also genes encoding for enzymes having aerostable α,β-enoate reductase activity towards molecules containing an α,β-enoate group and a primary amino group, can be applied in the process according to the present invention. For instance, the inventors have found that the *Escherichia coli* K12 (strain W3110) nemA gene (accession number: D86931), a gene that is known to have N-ethylmaleimide reductase activity, also has α,β-enoate reductase activity towards molecules containing an α,β-enoate group and a primary amino group. Such α,β-enoate reductase activity of the nemA gene has not been known so far. Based on sequence homology with the nemA gene from *E. coli*, other genes encoding for enzymes having aerostable α,β-enoate reductase activity towards molecules containing an α,β-enoate group and a primary amino group will be available from strains from, for instance, the genera *Agrobacterium, Escherichia, Pseudomonas, Salmonella, Shigella, Yersinia,* and *Vibrio*. All such further genes encoding for enzymes having aerostable α,β-enoate reductase activity towards molecules containing an α,β-enoate group and a primary amino group are, for the purposes of this patent application, considered to be equivalent to nemA.

Accordingly, the present invention also specifically relates to the following novel cells:

an *Escherichia coli* host cell in which the α,β-enoate reductase gene from *Ochrobactrum anthropi* NCIMB41200, or from *Acremonium strictum* CBS114157 is cloned and expressed;

a *Bacillus* host cell in which the α,β-enoate reductase gene from *Moorella thermoacetica* DSM1974, or from *Clostridium tyrobutyricum* DSM1460, or from *Ochrobactrum anthropi* NCIMB41200, or from *Acremonium strictum* CBS114157 is cloned and expressed;

a *Corynebacterium glutamicum* host cell in which the α,β-enoate reductase gene from *Moorella thermoacetica* DSM 1974, or from *Clostridium tyrobutyricum* DSM1460, or from *Ochrobactrum anthropi* NCIMB41200, or from *Acremonium strictum* CBS114157 is cloned and expressed;

an *Aspergillus niger* host cell in which the α,β-enoate reductase gene from *Acremonium strictum* CBS114157, or from *Moorella thermoacetica* DSM1974, or from *Clostridium tyrobutyricum* DSM1460, or from *Ochrobactrum anthropi* NCIMB41200 is cloned and expressed;

a *Pichia pastoris* host cell in which the α,β-enoate reductase gene from *Acremonium strictum* CBS114157, or from *Moorella thermoacetica* DSM1974, or from *Clostridium tyrobutyricum* DSM1460, or from *Ochrobactrum anthropi* NCIMB41200 is cloned and expressed; and a host cell selected from the group of *Aspergillus, Bacillus, Corynebacterium,* and *Pichia* host cells, in which the aerostable α,β-enoate reductase gene nemA from *E. coli* K12 is cloned and expressed.

In general, enzymes having aerostable α,β-enoate reductase activity are clearly preferred in the context for the present invention. That is because they can be expressed and used in microorganisms that are cultivated and/or used under aerobic conditions.

*Escherichia coli*, or *Bacillus*, or *Corynebacterium glutamicum*, or *Aspergillus niger* or *Pichia pastoris* host cells, in which the α,β-enoate reductase gene from *Moorella thermoacetica* DSM1974, or from *Clostridium tyrobutyricum* DSM1460, or from *Ochrobactrum anthropi* NCIMB41200, respectively from *Acremonium strictum* CBS114157 is cloned and expressed (or any such genes being homologous therewith and coding for enzymes having α,β-enoate reductase activity and capable of converting 6-AHEA into 6-ACA at an adequate degree), can be obtained by means of any suitable cloning strategy known to the skilled man, for instance, by the methods described in the experimental part hereof. Reference is also made to the well-known handbook of Sambrook, J., Fritsch, E. F., and Maniatis, T. Molecular Cloning: A Laboratory Manual. $2^{nd}$ ed., Cold Spring Harbor Laboratory, Cold Spring Harbor Laboratory Press, Cold Spring Harbor, N.Y., 1989. Similarly, such cloning strategies also can be applied for the construction of the aforementioned nemA clones (or clones equivalent therewith). Moreover, especially in cases where a gene originating from a fungus is cloned into a bacterial species, the skilled man will take appropriate measures to not only adapt the transcriptional and translational control sequences, but in addition use isolated or synthetically obtained cDNA sequences, in order to achieve functional expression of the enzyme to be produced.

The present invention, moreover, also relates to a process for precursor fermentation of 6-amino caproic acid (6-ACA) starting either from 6-aminohex-2-enoic acid (6-AHEA) or from 6-amino-2-hydroxyhexanoic acid (6-AHHA), and applying at least an enzymatic step with an enzyme having α,β-enoate reductase activity towards molecules containing an α,β-enoate group and a primary amino group, in particular with an enzyme having α,β-enoate reductase activity towards 6-aminohex-2-enoic acid.

In the most preferred embodiment, such precursor fermentation is performed in a microorganism wherein 6-aminohex-2-enoic acid (6-AHEA) is being formed in vivo. In fact, in such case, the formation of 6-ACA according to the present invention, is a biotransformation into 6-ACA starting from any suitable carbon source.

Carbon sources which can suitably be used in these specific embodiments of the process according to the invention are: oligosaccharides and disaccharides, for example maltose, β-galactoside, melibiose, epimelibiose, galactinol, melibitol, galactosylglycerol and trehalose, hexoses, for example D-glucose, D-fructose, D-mannose, L-sorbose and D-galactose, glucose containing solutions or slurries, starch, carbon source containing solutions or slurries, amino sugars, for example N-acetyl-D-glucosamine and D-glucosamine, methylpentoses, for example L-fucose and L-rhamnose, pentoses and trioses, for example L-arabinose, D-arabinose, D-xylose, xylitol, D-lyxose, D-ribose, 2-deoxy-D-ribose and dihydroxyacetone, pentoses in nucleosides and deoxynucleosides, for example cytidine, deoxycytidine, adenosine, deoxyadenosine, uridine, xanthosine, thymidine (deoxyuridine), purine (adenine, hypoxanthine, guanine ribonucleoside), hexuronides, hexuronates and hexonates, for example D-gluconate and D-galactonate, phosphorylated sugars and carboxylates, for example hexose phosphates, and sn-glycerol 3-phosphate, dicarboxylates, for example succinate, fumarate and L-malate, tricarboxylic acids, polyols, for example D-mannitol, D-glucitol, D-sorbitol, galactitol, dulcitol, D-arabitol, ribitol and xylitol, glycerol, two-carbon compounds, for instance ethanol and acetate, fatty acids, glycolate and glyoxylate, but also methanol, edible oils, or mixtures of any of the above compounds.

Most preferably, the 6-aminohex-2-enoic acid (6-AHEA) is being formed in vivo from a solution or slurry containing a suitable carbon source. Such suitable carbon sources may be selected from the group of glucose, glucose containing solutions or slurries, (m)ethanol, gluconate, pentoses, hexoses, starch and fatty acids. In particular, the carbon source used is glucose.

Because, as mentioned above, enzymes having enoate reductase activity towards 6-AHEA which are tolerant against free oxygen (and, thus can be said to be aerostable) are preferred in the context of the present invention (i.e. enzymes that can be expressed and used in microorganisms which are cultivated and/or used under aerobic conditions), preferably microorganisms are being used that can be used under aerobic conditions. The efficiency of growth (i.e. also of biomass production) under aerobic conditions, as well as the efficiency of production of relevant enzyme(s) and/or of substances to be produced, is generally much higher than for growth under anaerobic conditions. For instance, much better yields on glucose (or other carbon sources) are achieved. Such advantages are being described, for instance, in the general textbook "Allgemeine Mikrobiologie" of H. Schlegel, Thieme, Germany (1981).

Further the present invention relates to the novel, biochemically produced, substances as disclosed herein, and to products derived therefrom and having a $^{12}C$ versus $^{13}C$ versus $^{14}C$ isotope ratio of about the same value as occurring in environmental carbon dioxide, namely to biochemically produced 6-aminohex-2-enoic acid having a $^{12}C$ versus $^{13}C$ versus $^{14}C$ isotope ratio of about the same value as occurring in environmental carbon dioxide; biochemically produced 6-amino-hexanoic acid having a $^{12}C$ versus $^{13}C$ versus $^{14}C$ isotope ratio of about the same value as occurring in environmental carbon dioxide; ε-caprolactam having a $^{12}C$ versus $^{13}C$ versus $^{14}C$ isotope ratio of about the same value as occurring in environmental carbon dioxide, produced from biochemically produced 6-carboxy-6-aminohex-2-enoic acid, or 6-amino-hexanoic acid; and to nylon-6 and other derivatives having a $^{12}C$ versus $^{13}C$ versus $^{14}C$ isotope ratio of about the same value as occurring in environmental carbon dioxide, produced from biochemically produced 6-aminohex-2-enoic acid or 6-amino-hexanoic acid, or from ε-caprolactam that has been produced from biochemically produced 6-aminohex-2-enoic acid or 6-amino-hexanoic acid.

Each of these novel substances can be readily identified by means of methods as have been described above, for instance by Stable Isotope Ratio Mass Spectrometry (SIRMS) methods or by Site-Specific Natural isotope Fractionation studied by NMR. These novel substances are clearly different (namely in their $^{12}C$ versus $^{13}C$ versus $^{14}C$ isotope ratio) from the known substances of corresponding chemical structure and formula as have been obtained by chemical synthesis from fossil carbon sources and are being described in prior art references.

The invention will now be elucidated by means of the following experimental results, without, however, being restricted by any means to the methods or principles of this experimental part. It will, moreover, be clear that the present invention also will be applicable—by analogy—for the (bio) synthesis of higher α,ω-amino carboxylic acids from ω-amino 2-alkene carboxylic acids (and subsequent production of polyamides therefrom). For instance 11-amino-2-undecenoic acid could be a starting compound for the synthesis of polyamide-11. Embodiments for producing such higher α,ω-amino carboxylic acids by treatment of their corresponding α,β-unsaturated carboxylic acids are considered to be falling within the scope of the present claims.

I Preparation of 6-aminohex-2-enoic acid (6-ahea) from 4-aminobutyraldehyde diethylacetal The relevant reaction steps are described in R. Hamilton et al, Tet. Letters 1993 (34), p. 2847-2850; in P. Hughes et al., J. Org. Chem. 1994 (59), p. 5799-5802; and in C. Stammer et al., J. Org. Chem. 1969 (34), p. 2306-2311, respectively.

4-Aminobutyraldehyde diethylacetal (technical, 90%; 202.4 g, 1130 mmol) and phthalic anhydride (186 g, 1256 mmol) were reacted under Dean-Stark conditions for 4 h in toluene (1700 ml), containing about 10 wt. % of triethylamine (TEA; 166 g, 1640 mmol). After cooling to room temperature (RT) the solvent and excess of TEA were evaporated in vacuo. The residue was dissolved and refluxed for 20 min. in a mixture of 2M aqueous HCl (2000 ml) and acetone (2800 ml). After cooling to RT the acetone was removed in vacuo and the residue was extracted with $CH_2Cl_2$ (5×200 ml). The organic phase was washed with 2M aqueous HCl (3×200 ml) and with saturated aqueous $NaHCO_3$ (2×200 ml). After drying of the solution over $Na_2SO_4$ the 4-phtalimidobutanal was isolated by evaporating the $CH_2Cl_2$ in vacuo. After drying in an exsiccator over $P_2O_5$ in vacuo 240.5 g of 4-phtalimidobutanal were obtained (yield: 98%).

4-Phthalimidobutanal (120.9 g, 556 mmol) was then dissolved in 600 ml of $CH_2Cl_2$ and treated with methyl(triphenylphosphoranylidene)acetate (186 g, 556 mmol) in 600 ml of $CH_2Cl_2$. After 1 h the mixture was concentrated in vacuo and chromatographed in seven equal portions (Merck Kieselgel 60; 7×14 cm column; eluent 30% ethyl acetate in hexane) to give 145.6 g (96%) of methyl-6-phtalimidohex-2-enoate as a white solid.

Methyl-6-phtalimidohex-2-enoate (145.6 g; 533 mmol) was dissolved in methanol (900 ml) and stirred with 71.6 g NaOH (1790 mmol) in 1700 ml of distilled water at RT for 8 h. The solution was treated with charcoal and filtered. The filtrate was acidified with 260 ml of 37% aqueous HCl and then refluxed for 3 h. After cooling to RT a small amount of precipitate was filtered off and the solution was concentrated in vacuo until crystallization began. The precipitate was filtered off and the solution was evaporated to dryness in vacuo. The residue was boiled with a 7:1 (vol/vol) mixture of 2-propanol and ethyl acetate (2×800 ml) in order to extract the product. After filtration the solvents were evaporated in vacuo and the residue was recrystallized from 2-propanol (385 ml) to give 36.7 g (42%) of 6-amino-hex-2-enoic acid HCl salt.

The NMR data for 6-AHEA, measured using 250 MHz NMR in $CD_3OD$, were as follows:

| Protons | Chemical shift (ppm) | d = doublet,<br>t = triplet, q = quartet |
|---------|---------------------|------------------------------------------|
| b | 6.93 | d × t |
| a | 5.88 | d |
| e | 2.95 | t |
| c | 2.34 | q |
| d | 1.84 | quintet |

Protons a, b, c, d, and e are located, respectively, at the $\alpha$, $\beta$, $\gamma$, $\delta$, and $\epsilon$ carbon atom.

II Media and Preparation Thereof

II.1 PYG Medium (Non-Selective):

To 1 l deionized water is added: 1.25 g pepton, 1.25 g yeast extract and 3 g glucose; pH is adjusted to pH 5.8. Divide over penicillin bottles (50 ml medium in 100 ml bottle), heat (by placing in a boiling water bath, but without boiling the samples in the bottles) to remove $O_2$ and flush (through the medium, and under slight $N_2$ overpressure above the medium) with $N_2$. Sterilize at 121° C. for 15 minutes. Optionally last traces of $O_2$ may be removed by adding 0.05% of sterile sodium thioglycolate.

II.2 Selective Medium (Crotonate Medium; (According to F. Rohdich et al., J. Biol. Chem. 276(6), 5779-5787 (2001); and Bader, J. et al., Hoppe-Seyler's Z. Physiol. Chem., Bd. 359, pages 19-27, (1978)):

To 1 liter deionized water is added: 6 g crotonic acid, 0.3 g NaOH, 150 mg $(NH_4)_2HPO_4$, 100 mg $K_2HPO_4$, 33 mg $MgCl_2.6H_2O$, 50 mg $NH_4Cl$, 1 g yeast extract, 1 g tryptic caseine, 40 mg $CaCl_2.2H_2O$, 0.4 mg $MnSO_4.2H_2O$, 0.4 mg $FeSO_4.2H_2O$, 10 mg $(NH_4)_6MO_7O_{24}.4H_2O$, 0.04 mg biotin, 0.8 mg p-aminoben 0.5 mg resazurin, 8 ml 50% $K_2CO_3$ and 0.05% sodium thioglycolate.

All ingredients (except for the vitamin-, $K_2CO_3$— and sodium thioglycolate solution) were mixed and divided over some penicillin bottles (50 ml in 100 ml bottles). After this, the bottles were flushed with a stream of $N_2$ and sterilized (for 15 minutes at 121° C.). Subsequently, a sterilized and $O_2$-free mixture of the other compounds was added. The pH was checked and, if needed, additional sterile $K_2CO_3$ solution was added to adjust the pH to about pH 6.4.

For larger scale (500 ml cultures) the same procedure was followed, except for the procedure for the addition of crotonate and $FeSO_4$. According to Arch. Microbiol, 127, 279-287 (Bader, J. et al. (1980)) the amount of enoate reductase increases if an optimal cultivation procedure is followed i.e. starting with 35 mM crotonate instead of 70 mM and $1.8*10^{-5}$ M $FeSO_4$. When the culture becomes stationary, 35 mM crotonate and $2*10^{-5}$ M $FeSO_4$ are added. The best time to harvest the cells is 12 h after stationary growth phase.

II.3 Medium for E. coli TOP10 Clones:

A rich medium, Luria Bertani medium (LB-medium; also called Luria broth or Lenox broth; containing per 1:10 g bacto tryptone, 5 g yeast extract and 5 g NaCl), under $N_2$ atmosphere, was used for cultivation of E. coli TOP10/pBAD-Ctyr (1)-enr-DEST, E. coli TOP10/pBAD-Mther(1)-enr-DEST, and E. coli TOP10/pBAD-nemA_Eco. Each medium contains an appropriate antibiotic, as indicated in part III below.

II.4 Cultivation Conditions:

C. tyrobutyricum DSM1460 was cultivated, under anaerobic conditions ($N_2$ atmosphere), on selective medium (see above).

M. thermoacetica DSM1974 was cultivated, under anaerobic conditions ($N_2$ atmosphere), on non-selective (PYG) medium (see above).

C. tyrobutyricum DSM1460 was incubated at 37° C., and Moorella thermoacetica DSM1974 at 55-60° C.

E. coli TOP10/pBAD-Ctyr(1)-enr-DEST and E. coli TOP10/pBAD-Mther(1)-enr-DEST were cultivated under anaerobic conditions ($N_2$ atmosphere), at 28° C.

E. coli TOP10/pBAD-nemA_Eco was cultivated under aerobic conditions, at 28° C.

III Construction of Vectors and Plasmids

III.1 General Procedures

Standard molecular cloning techniques such as plasmid DNA isolation, gel electrophoresis, enzymatic restriction modification of nucleic acids, E. coli transformation etc. were performed as described by Sambrook, J., Fritsch, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989 or the supplier's manual. Standard molecular cloning enzymes such as restriction endonucleases, T4 DNA ligase, etc. were obtained from Invitrogen (Breda, The Netherlands) unless otherwise stated. Synthetic oligodeoxynucleotides were obtained from Sigma-Genosys (Cambridge, UK), and Invitrogen (Paisley, Scotland, UK). DNA sequence analyses were performed by BaseClear (Leiden, The Netherlands) using the chain termination method with dye-labeled dideoxy-terminators.

III.2 Construction of Gateway™ Destination Vector pBAD/Myc-His-DEST

Destination vector pBAD/Myc-His-DEST, that was used for the expression of the enoate reductase genes from Clostridium tyrobutyricum DSM1460 and Moorella thermoacetica DSM1974 in E. coli as well as for the N-ethylmaleimide reductase gene (nemA) from Escherichia coli K12 in E. coli TOP10, was prepared by introducing a cat/ccdB cassette into the commercially available E. coli expression vector pBAD/Myc-HisC. The cat/ccdB cassette was amplified by PCR using

[SEQ ID: No.1]
5'-AAGAAGACCGGATCCTAC<u>CTGACGCTTTTTATCGCAACTCTCTACTG</u>-

TTTCTCCATACCCGTTTTTGGGCTAACACAAGTTTGTACAAAAAAGCTG-

AAC-3' as forward primer (with promoter sequence double underlined, Bpi I recognition and cleavage site underlined and attR sequences in italics), and

[SEQ ID. No.2]
5'-TTGTT<u>CTACGTA</u>ACCACTTTGTACAAGAAAGCTGAAC-3' as reverse primer (with SnaB I cleavage site underlined and attR sequences in italic), and vector pDEST15 (Invitrogen) as template. The PCR, which was performed with Expand High Fidelity polymerase (Roche Applied Science, Mannheim, Germany) according to the supplier's protocol, yielded a single fragment. Correct size (1792 bp) of the amplified fragment was confirmed by agarose gel electrophoresis. After purification of the amplified fragment from a preparative agarose gel with the QIAquick Gel Extraction Kit (QIAGEN GmbH, Hilden, Germany), the fragment was digested to completion with Bpi I (MBI Fermentas, St.Leon-Rot, Germany) (resulting in a overhang complementary to BamH I) and SnaB I (New England Biolabs, Frankfurt, Germany) and ligated with T4 DNA ligase into the *E. coli* expression vector pBAD/Myc-HisC (Invitrogen), which had been digested with BamH I and SnaB I. The ligation mix was subsequently used to transform Chemically Competent *E. coli* DB3.1 cells (Invitrogen). Recombinant cells were selected by plating the whole transformation mixture on 2*TY plates containing 35 µg/ml chloramphenicol followed by overnight incubation at 37° C. After isolation of the recombinant plasmid from three individual colonies, the inserts were sequenced. One of these clones proved to contain the desired insert, and was named pBAD/Myc-His-DEST. Although 7 aberrations were observed between the nucleotide sequence of the sequenced part of plasmid pBAD/Myc-His-DEST and the reference sequence (Invitrogen—nucleotide sequence of pDEST15), all the essential features (chloramphenicol resistance, ccdB selection and attR recombination) of pBAD/Myc-His-DEST were fully functional.

III.3 Construction of Plasmid pBAD-Ctyr(1)-enr-DEST

The *C. tyrobutyricum* enoate reductase gene was cloned into *E. coli* expression vector pBAD/Myc-His-DEST using PCR and Gateway™ Technology (Invitrogen Corp., Carlsbad, Calif., USA) for cloning. The enoate reductase open reading frame was first PCR amplified using

[SEQ ID: No.3]
5'-<u>GGGACAAGTTTGTACAAAAAAGCAGGCT</u>AGGAGGAATTAACC*ATG*AA-

AAACAAATCTTTATTTGAACC-3' as forward primer (with Shine-Delgarno site underlined, ATG start codon in italic and attB1 site double underlined) and

[SEQ ID: No.4]
5'-<u>GGGGACCACTTTGTACAAGAAAGCTGGGT</u>*CTA*ACAGTTAAGTCCAAT-

TTCATTTCC-3' as reverse primer (with stop codon in italics and attB2 site double underlined), and genomic DNA as template. The start codon was changed (GTG towards ATG).

The genomic DNA was isolated following a universal protocol using Promega products. For this, 50 ml selective crotonate medium was inoculated with *C. tyrobutyricum*, followed by subsequent growth overnight at 28° C. During the last half h of this growth carbenicillin (final concentration 200 µg/ml) was added to weaken the cell wall. All cells were harvested by centrifugation, and the received pellet was resuspended in 2.5 ml 50 mM Tris-HCl, pH 8.0 containing 50 mM EDTA. After addition of 50 μl lysozyme (100 mg/ml) and 12.5 μl proteinase K (20 mg/ml) the suspension was incubated for 30 minutes at 37° C. Addition of 3 ml Nuclei Lysis Solution (Promega Corporation, Madison, USA) followed by incubation for 15 minutes at 80° C. led to complete lysis. After RNase treatment (final concentration of 4 μg/ml) incubated for 30 minutes at 37° C., 1 ml Protein Precipitation Solution (Promega Corporation, Madison, USA) was added, and the solution was vortexed for 20 seconds and incubated on ice for 15 minutes. After centrifugation (15 minutes at 4000×g, 4° C.), the supernatant was transferred to a mixture of 0.1 volumes NaAc (3M, pH 5) and 2 volumes absolute ethanol. The precipitated DNA was collected by centrifugation (14000×g for 15 minutes at 4° C.). Finally, the pellet was dissolved in 1 ml 10 mM Tris-HCl (pH 8).

The PCR, which was performed with PCR Supermix High Fidelity (Invitrogen) according to the supplier's protocol, yielded a single fragment. Correct size (2076 bp) of the amplified fragment was confirmed by agarose gel electrophoresis.

After purification of the amplified fragment PCR purification kit of QIAGEN GmbH, the fragment was used as a substrate for the so-called BP in-vitro recombination reaction, which was performed according to the Gateway™ manual of the supplier (Invitrogen). Recombination between the attB-PCR fragment and the pDONR201 Donor Vector and subsequent transformation of the obtained mixture into *E. coli* TOP10 competent cells (Invitrogen) resulted in the ENTRY clone pDONR-Ctyr(1)enr. Recombinant cells were selected by plating the whole transformation mixture on LB plates containing 50 μg/ml of kanamycin, followed by cultivation at 20° C. over the weekend. All colonies were collected from the LB agar plate and plasmid DNA was isolated using the QIAprep Spin Miniprep Kit (QIAGEN GmbH).

Subsequently, the enoate reductase containing PCR fragment was introduced in Destination vector pBAD/Myc-His-DEST (vide infra) via the so-called LR in-vitro recombination reaction using a mixture of pDONR-Ctyr(1)enr clones and pBAD/Myc-His-DEST. Also this reaction was performed according to the supplier's procedure. The recombination mix was used to transform One Shot™ Chemically Competent *E. coli* TOP10 Cells (Invitrogen). Recombinant cells were selected by plating the whole transformation mixture on LB agar plates containing 100 μg/ml carbenicillin followed by overnight incubation at 28° C. After overnight cultivation of 16 colonies in LB medium containing 100 μg/ml carbenicillin, plasmid DNA was isolated using the QIAprep Spin Miniprep Kit (QIAGEN GmbH). Digestion with restriction enzymes Acc I and Rsr II, respectively, proved that 11 of the 16 tested colonies contained the desired recombinant plasmid pBADCtyr(1)enr-DEST.

A single colony of strain *E. coli* TOP10/pBAD-Ctyr(1)enr-DEST was used to inoculate under $N_2$ atmosphere 5 ml LB medium supplemented with 50 mM potassium phosphate and 100 μg/ml carbenicillin. After overnight growth, 2.5 ml of this preculture was used to inoculate 500 ml of the same medium under $N_2$ atmosphere. When, after a few h incubation at 28° C., an $OD_{620\ nm}$ of 0.4 was reached, 0.005% arabinose was added to start the induction. After overnight incubation at 28° C., cells were harvested via centrifugation (10 min. at 4000× g, 4° C.). After resuspending the cell pellets in oxygen-free potassium phosphate buffer (100 mM, pH 7.0) with about one weight volume buffer, cell pellets were stored at −20° C., until use in bioconversion reactions.

III.4 Construction of Plasmid pBAD-Mther(1)-enr-DEST

The *Moorella thermoacetica* enoate reductase gene was subcloned into *E. coli* expression vector pBAD/Myc-His-DEST using PCR and Gateway™ Technology (Invitrogen). The enoate reductase open reading frame was first PCR amplified using

[SEQ ID: No.5]
5'-GGGACAAGTTTGTACAAAAAAGCAGGCTAGGAGGAATTAACC*ATG*GT-

AGCCTATACCAGACTTTTTG-3' as forward primer (with Shine-Delgarno site underlined, ATG start codon in italic and attB1 site double underlined, and

[SEQ ID: No.6]
5'-<u>GGGGACCACTTTGTACAAGAAAGCTGGGT</u>*CTAAATCCCTCGCCCTAC CTC*-3' as reverse primer (with stop codon in italics and attB2 site double underlined), and genomic DNA as template. The start codon was changed (GTG towards ATG).

The genomic DNA was isolated following a universal protocol using Promega products. For this, *Moorella thermoacetica* was isolated from glycerol stock made after growth on PYG medium. All cells were harvested by centrifugation, and the received pellet was resuspended in 0.25 ml 50 mM Tris-HCl, pH 8.0 containing 50 mM EDTA. After addition of 0.5 µl lysozyme (100 mg/ml) and 1.25 µl proteinase K (20 mg/ml) the suspension was incubated for 30 minutes at 37° C. Addition of 0.3 ml Nuclei Lysis Solution (Promega Corporation, Madison, USA) followed by incubation for 15 minutes at 80° C. led to complete lysis. After RNase treatment (final concentration of 4 µg/ml) and incubation for 30 minutes at 37° C., 1 ml Protein Precipitation Solution (Promega Corporation, Madison, USA) was added, and the solution was vortexed for 20 seconds and incubated on ice for 15 minutes. After centrifugation (15 minutes at 4000×g, 4° C.), the supernatant was transferred to a mixture of 0.1 volumes NaAc (3M, pH 5) and 2 volumes absolute ethanol. The precipitated DNA was collected by centrifugation (at 14000×g for 15 minutes; at 4° C.). Finally, the pellet was dissolved in 0.05 ml 10 mM Tris-HCl (pH 8).

The PCR, which was performed with PCR Supermix High Fidelity (Invitrogen) according to the supplier's protocol, yielded not in enough fragments. However, after a second PCR enough PCR fragments were received. Furthermore, the correct size (2045 bp) of the amplified fragment was confirmed by agarose gel electrophoresis.

After purification of the amplified fragment PCR purification kit of QIAGEN GmbH, the fragment was used as a substrate for the so-called BP in-vitro recombination reaction, which was performed according to the Gateway™ manual of the supplier (Invitrogen). Recombination between the attB-PCR fragment and the pDONR201 Donor Vector and subsequent transformation of the obtained mixture into *E. coli* TOP10 competent cells (Invitrogen) resulted in the ENTRY clone pDONR-Mther(1)enr. Recombinant cells were selected by plating the whole transformation mixture on LB plates containing 50 µg/ml of kanamycin, followed by cultivation at 20° C. over the weekend. All colonies were collected from the LB agar plate and plasmid DNA was isolated using the QIAprep Spin Miniprep Kit (QIAGEN GmbH).

Subsequently, the enoate reductase containing PCR fragment was introduced in Destination vector pBAD/Myc-His-DEST (vide infra) via the so-called LR in-vitro recombination reaction using a mixture of pDONR-Mther(1)enr clones and pBAD/Myc-His-DEST. Also this reaction was performed according to the supplier's procedure. The recombination mix was used to transform One Shot™ Chemically Competent *E. coli* TOP10 Cells (Invitrogen). Recombinant cells were selected by plating the whole transformation mixture on LB agar plates containing 100 µg/ml carbenicillin followed by overnight incubation at 28° C. After overnight cultivation of 16 colonies in LB medium containing 100 µg/ml carbenicillin, plasmid DNA was isolated using the QIAprep Spin Miniprep Kit (QIAGEN GmbH). Digestion with restriction enzymes XmaI and BamHI, respectively, proved that 4 of the 16 tested colonies contained the desired recombinant plasmid pBAD-Mther(1)enr-DEST.

A single colony of strain *E. coli* TOP10/pBAD-Mther(1) enr-DEST was used to inoculate under $N_2$ atmosphere 5 ml LB medium supplemented with 50 mM potassium phosphate and 100 µg/ml carbenicillin. After overnight growth, 2.5 ml of this preculture was used to inoculate 500 ml of the same medium under $N_2$ atmosphere.

When, after a few h incubation at 28° C., an $OD_{620\,nm}$ of 0.4 was reached, 0.005% arabinose was added to start the induction. After overnight incubation at 28° C., cells were harvested via centrifugation (10 min. at 4000×g, 4° C.). After resuspending the cell pellets in oxygen-free potassium phosphate buffer (100 mM, pH 7.0) with about one weight volume buffer, cell pellets were stored at −20° C., until use in bioconversion reactions.

III.5 Construction of Plasmid pBAD-nemA_Eco

The *Escherichia coli* K12 (strain W3110) nemA gene (accession number: D86931) for N-ethylmaleimide reductase was cloned into *E. coli* expression vector pBAD/Myc-His-DEST using PCR and Gateway™ Technology (Invitrogen). The nemA open reading frame was first PCR amplified using

[SEQ ID: No.7]
5'-<u>GGGGACAAGTTTGTACAAAAAAGCAGGCT</u>*AGGAGGA*ATTAACC*ATGT*-CATCTGAAAAACTGTATTCCCC-3' as forward primer (with Shine-Delgarno site underlined, ATG start codon in italic and attB1 site double underlined, and

[SEQ ID: No.8]
5'-<u>GGGGACCACTTTGTACAAGAAAGCTGGGT</u>*TTACAACGTCGGGTAATCG GTATAGC*-3' as reverse primer (with stop codon in italics and attB2 site double underlined), and genomic DNA of *Escherichia coli* K12 (strain W3110) as template.

The PCR, performed with AccuPrime Pfx DNA Polymerase (Invitrogen) according to the supplier's protocol, yielded a single product fragment. Correct size (1169 bp) of the amplified fragment was confirmed by agarose gel electrophoresis.

After purification of the amplified fragment using the PCR purification kit of QIAGEN GmbH, the fragment was used as a substrate for the so-called BP in-vitro recombination reaction, which was performed according to the Gateway™ manual of the supplier (Invitrogen). Recombination between the attB-PCR fragment and the pDONR201 Donor Vector and subsequent transformation of the obtained mixture into *E. coli* DH5α competent cells (Invitrogen) resulted in the ENTRY clone pENTR-nemA_Eco. Recombinant cells were selected by plating the whole transformation mixture on LB plates containing 50 µg/ml of kanamycin, followed by cultivation at 20° C. over the weekend. All colonies were collected from the LB agar plate and plasmid DNA was isolated using the QIAprep Spin Miniprep Kit (QIAGEN GmbH).

Subsequently, the nemA containing fragment was introduced in Destination vector pBAD/Myc-His-DEST (vide infra) via the so-called LR in-vitro recombination reaction using a mixture of pENTR-nemA_Eco clones and pBAD/Myc-His-DEST. Also this reaction was performed according to the supplier's procedure. The recombination mix was used to transform One Shot™ Chemically Competent E. coli TOP10 Cells (Invitrogen). Recombinant cells were selected by plating the aliquots of the transformation mixture on LB agar plates containing 100 µg/ml carbenicillin followed by overnight incubation at 28° C. After overnight cultivation of 3 clones in LB medium containing 100 µg/ml carbenicillin, plasmid DNA was isolated using the QIAprep Spin Miniprep Kit (QIAGEN GmbH). Digestion with restriction enzymes EcoRV and FspI, respectively, proved that all tested colonies contained the desired recombinant plasmid pBAD-nem-A_Eco.

Additionally these clones of strain E. coli TOP10/pBAD-nemA_Eco were used to inoculate 50 ml LB medium supplemented with 100 µg/ml carbenicillin in sterile 500 ml Erlenmeyer flasks to a cell density of $OD_{620}$ of 0.05. These 50 ml cultures were incubated at 28° C. on an orbital shaker with 180 rotations per minute (rpm). At an $OD_{620\ nm}$ of 0.6, 0.02% arabinose was added to start the induction. After overnight incubation at 28° C., cells were harvested via centrifugation (10 min. at 4000×g, 4° C.). After resuspending the cell pellets in 2 ml potassium phosphate buffer (100 mM, pH 7.0), cell pellets were stored at −20° C. in 1 ml portions until further use.

Cells were subsequently disrupted by sonification (using an MSE Soniprep 150 with a small nozzle; 10 seconds of sonification with an altitude of 5-10 microns followed by 10 seconds break. The total cycle lasted 5 minutes. During this procedure the solution was kept cool using an acetone-ice bath.). The disrupted cells were centrifuged (16,000×g for one hour) and the cell free extract was stored at 4° C. until the assay for reduction of 6-ACA was performed.

IV Analytical Methods

Depending of the components to be analysed, some different HPLC (High Performance Liquid Chromatography) methods, and LC-MS (Liquid Chromatography coupled with Mass Spectrometry), using mutiple stage MS techniques as $MS^2$-SRM (Selective Reaction Monitoring) and/or $MS^3$-CRM (Consecutive Reaction Monitoring), were used, the conditions of which are being shown below.

IV.a. HPLC-Analysis for Measuring of 6-AHEA and 6-ACA
Column: Prevail C18 from Alltech (250 mm×4.6 mm I.D., 5µ)
Column temperature: Ambient (±22° C.)
Flow: 1.0 ml/min.
Injection volume: 20 or 100 µl (higher sensitivity of the method at 100 µl)
Run time: 20 to 40 min.
  (depending on the background of the matrix, i.e. longer run time in case more side peaks present)
Eluent: 100 mM perchloric acid in water pH 1.0
  (16.3 g 70% perchloric acid/liter water)
Sample solution: Eluent
Detection: Post column reaction/fluorescence (simultaneously at $\lambda$ex 338 nm/$\lambda$em >420 nm) (Post column reaction with ortho-phthalic aldehyde/mercaptoethanol (OPA/MCE), ambient temperature, at 1.0 ml/min.).
Retention times: 14.2 minutes for 6-ACA; 11.7 minutes for 6-AHEA.

IV.b1. $LC-MS^2$-Analysis was Used Under the Following LC-, resp. MS-Conditions
Equipment: LCQ ion trap mass spectrometer from Thermo Finnigan.
LC Column: 250×4.6 mm Prevail C18 (Alltech)
Eluent: 0.025% (v/v) formic acid in water (pH 3.2)
Flow: 1 ml/min. before entering the MS the flow is split 1:5
Inj. Vol.: 100 µl.
MS Electrospray in positive ion mode: in $LC-MS^2$-SRM mode (a highly selective and sensitive analysis), with MS conditions as follows:
Ionization: Positive ion electrospray

| Source conditions: | sheath gas: | 60 |
| --- | --- | --- |
| | aux/sweep gas: | 25 |
| | spray voltage: | 5 kV |
| | capillary temperature: | 300° C. |
| | capillary voltage: | 5 V |
| | tube lens offset: | 25 V |
| Scan event: | parent mass: | 132.0 |
| | isolation width: | 1.1 amu |
| | norm. collision energy: | 28% |
| | activation Q: | 0.250 |
| | activation energy: | 30 msec. |
| | SRM range: | 114, width 1.2 (113.4-114.6 amu). |

IV.b2. $LC-MS^3$-analysis was Used (in other Analyses, as Indicated Below) Under the Following LC-, resp. MS-Conditions, Differing from those Mentioned in IV.b1.
Equipment: HP1100 LC system (Agilent Technologies) coupled to a LCQ
Deca XP ion trap mass spectrometer from Thermo Finnigan.
LC Column: 50×4.6 mm Nucleosil 120-5 C18 (Machery & Nagel) in series with 150×4 mm Atlantis dC18, 5 µm (Waters)
Column temperature: ambient (±22° C.)
Eluent: 0.025% (v/v) formic acid +1% acetonitrile in water (pH 3.2)
Flow: 1 ml/min, before entering the MS the flow is split 1:5
Inj. Vol.: 2 µl.
MS CRM (Consecutive Reaction Monitoring) mode (a highly selective and sensitive mode of analysis) was used to selectively detect the 6-ACA, with MS conditions as follows:

| Ionization technique | positive ion electrospray | |
| --- | --- | --- |
| Source conditions: | sheath gas: | 60 |
| | aux/sweep gas: | 10 |
| | spray voltage: | 4 kV |
| | capillary temperature: | 330° C. |
| | capillary voltage: | 5 V |
| | tube lens offset: | 15 V |
| Scan mode CRM: | $MS^1$: parent mass | 132.0 |
| | isolation width: | 1.0 amu |
| | norm. collision energy: | 26% |
| | $MS^2$: parent mass | 114.0 |
| | isolation width: | 1.0 amu |
| | norm. collision energy: | 26% |
| | CRM ranges: | 78.5-79.5 and 95.5-96.5 amu |

Under the chromatographic conditions as described in IV.b1. 6-ACA eluted at 3.5 minutes. 6-ACA then was determined quantitatively using the chromatographic conditions under IV.b2 combined with the mass spectrometric SRM conditions as described under IV.b.1. The presence of 6-ACA in positive samples from the SRM analysis is confirmed by performing the CRM $MS^3$ experiment and checking the presence and intensity ratio of ions m/z 79 and 96.

IV.c. GC-MS-Analysis was Performed in Most of the Analyses, Using a HP6890 Gas Chromatograph Under the Following GC-, resp. MS-Conditions

| GC conditions: | |
| --- | --- |
| GC type: | HP6890 GC + Ata Focus autosampler |
| Column type: | CPSIL8CB, Low Bleed/MS |
| Column dimensions: | 30 m × 0.25 mm i.d. × 1.0 μl |
| Oven temperature: | 60° C. (1 min) → 20° C./min → 280° C. (0 min) |
| Column flow: | 1.2 ml/min, helium, constant flow |
| Injection type: | Splitless (splitless time 1 min) |
| Liner: | Altech (art. 4928) filled with a plug of deactivated glass wool |
| Injection temperature: | 300° C. |
| Injection volume: | 0.5 μl |
| MS conditions: | |
| MS type: | HP5973 MSD |
| MS source temperature: | 230° C. |
| MS quad temperature: | 150° C. |
| Aux temperature: | 250° C. |
| Scan mode: | SIM, m/z 113 |

V Bioconversions

V.(a) Bioconversion of 6-AHEA to 6-ACA by *C. tyrobutyricum*; Analysis by HPLC:

$O_2$-free buffer (100 mM potassium phosphate, pH 6.0) was transferred into penicillin bottles under a stream of nitrogen in a glove box. The bottles were closed with butyl rubber stoppers. After this, reactions were started by injection of substrate 6-AHEA (100 mM stock solution; adjusted to pH 6) and/or cells (cell pellets of *C. tyrobutyricum* stored at −20° C., and resuspended in 100 mM potassium phosphate, pH 7) through the stopper. Finally, NADH was added (110 μl of a 5 mM stock solution). The reaction mixture (total volume of 2.3 ml) consisted of potassium phosphate buffer (100 mM, pH 6.0), 5 mM 6-amino-hex-2-enoic acid and 0.23 mM NADH.

Furthermore, a blanc cell mixture (without substrate) and a chemical blanc mixture (without cells) were made. All reaction bottles were incubated at 37° C. At different time intervals 0.5 ml samples were taken, from which cells were subsequently removed by centrifugation (Eppendorf 5415 C centrifuge, 10 minutes, max. rpm, 4° C.) and the samples were stored at −20° C. till analysis. Just before HPLC analysis, samples were diluted 5 to 10 times with eluent (100 mM perchloric acid in water pH 1.0). Results are summarized in Table 1.

TABLE 1

6-ACA formation by bioreduction of
6-AHEA by *Clostridium tyrobutyricum* cells.

| Time (h) | Concentration 6-ACA (ppm) |
| --- | --- |
| 0 | <0.1 |
| 24 | 1.0 |
| 48 | 1.7 |

Table 1 shows that *Clostridium tyrobutyricum* can perform the bioreduction of 6-AHEA to 6-ACA. The concentration of 6-ACA increases in time. No 6-ACA could be observed in the blanc cell mixture or in the chemical blanc mixture. The chemical identity of the product 6-ACA was confirmed with LC-MS-MS using selective reaction monitoring at the source conditions and scan event as described in IV.b.

V.(b) Bioconversion of 6-AHEA to 6-ACA by *E. coli* pBAD-Ctyr(1)-enr-DEST and *E. coli* pBAD-Mther(1)-enr-DEST; Analysis by HPLC and LC-MS-MS SRM An $O_2$-free solution of 6-AHEA (20 mM in 100 mM potassium phosphate buffer, pH 6.0) was transferred into penicillin bottles under a stream of nitrogen in a glove box. The bottles were closed with butyl rubber stoppers. Hereafter, reactions were started by injection of cells (cell pellets stored at −20° C., resuspended in 100 mM potassium phosphate buffer pH 7.0) and NADH solution through the stopper. The reaction mixture (having a total volume of about 3 ml) contained potassium phosphate buffer (100 mM, pH 6.0), 20 mM 6-AHEA and 0.23 mM NADH.

Furthermore, a blanc cell mixture (without substrate) and a chemical blanc mixture (without cells) were performed. After 44 h of incubation 0.5 ml samples were taken, from which cells were subsequently removed by centrifugation (Eppendorf 5415 R centrifuge, 14,000 rpm, 10 min., 4° C.) and the samples were stored at −20° C. till analysis. Just before HPLC analysis, samples were diluted 5 to 10 times with HPLC eluent (100 mM perchloric acid in water pH 1.0) and just before LC-MS-MS analysis, samples were diluted 5 to 10 times with MS eluent (0.025% (v/v) formic acid in water (pH 3.2)). Results are summarized in table 2.

TABLE 2

6-ACA formed by bioreduction of 6-AHEA by the
enoate reductase clones *E. coli* pBAD-Ctyr(1)-enr-DEST
and *E. coli* pBAD-Mther(1)-enr-DEST.

| Sample | 6-ACA conc, measured by HPLC (ppm) | 6-ACA conc, measured by LC-MS-MS SRM (ppm) |
| --- | --- | --- |
| *E. coli* pBAD-Ctyr(1)-enr-DEST | 12 | 11 |
| *E. coli* pBAD-Mther(1)-enr-DEST | 31 | 29 |

Table 2 shows that both *E. coli* pBAD-Ctyr(1)-enr-DEST and *E. coli* pBAD-Mther(1)-enr-DEST perform the bioreduction of 6-AHEA to 6-ACA. No 6-ACA could be observed in the blanc cell mixture or in the chemical blanc mixture.

V.(c) Bioconversion of 6-AHEA to 6-ACA by *E. coli* TOP10/pBAD-nemA_Eco; Analysis by LC-$MS^3$ CRM A reaction mixture consisting of 100 mM Tris-buffer, pH 7.5, including 20 mM glucose, 5 mM 6-AHEA, 7.0 mM NADPH, 7.0 mM NADH, and 10 U/ml glucose oxidase, was prepared. To start the bioconversion of 6-AHEA to 6-ACA 400 μl cell free extract of *E. coli* TOP10/pBAD-nemA_Eco was added (total reaction volume 1 ml). After 23 h and 48 h 250-300 μl samples were taken for LC-$MS^2$ SRM analysis. Furthermore, a chemical blanc mixture (without cell free extract) was incubated under the same conditions and sampled after the same incubation times. Results are summarized in table 3.

TABLE 3

6-ACA formation by bioreduction of 6-AHEA by cell
free extract of *E. coli* TOP10/pBAD-nemA_Eco.

| Time (h) | 6-ACA concentration (in ppm) measured by LC-$MS^3$ CRM |
| --- | --- |
| 23 | 0.6 |
| 48 | 0.9 |

Table 3 shows that cell free extract of *E. coli* TOP10/pBAD-nemA_Eco performs the bioreduction of 6-AHEA to 6-ACA. No 6-ACA could be observed in the chemical blanc mixture.

Confirmation of 6-ACA in these samples was carried out by determining the presence and intensity ratio of the MS³ fragment ions with m/z 96 and 79 as determined in the CRM analysis and comparing the ratio's with those from a calibration standard 6-ACA treated in the same manner. Results are summarized in Table 4.

TABLE 4

Intensity ratio's for fragment ions m/z 96 and 79 from the CRM analyses

| Time (h) | Intensity ratio m/z 96: m/z 79 |
|---|---|
| 23 | 3 |
| 48 | 3 |
| calibration sample | 3 |

VI Biotransformation of 6-AHEA into 6-ACA; Cyclization of 6-ACA

An $O_2$-free solution of 6-AHEA (20 mM in 100 mM potassium phosphate buffer, pH 6.0) was transferred into penicillin bottles under a stream of $N_2$ in a glove box. The bottles were closed with butyl rubber stoppers. Hereafter the biotransformation was started by injection of cells of the enoate reductase clone *E. coli* pBAD-Ctyr(1)-enr-DEST (cell pellets stored at −20° C., resuspended in 100 mM potassium phosphate buffer, pH 7.0) and NADH solution through the stopper. The reaction mixture, having a total volume of about 3 ml, contained potassium phosphate buffer (100 ml, pH 6.0), 20 mM 6-AHEA and 0.23 mM NADH.

After 44 h of incubation a sample of 0.5 ml was taken, from which cells were removed by centrifugation (Eppendorf 5415 R centrifuge; 14,000 rpm; 10 min.; 4° C.) and the sample was stored at −20° C. until cyclization of the 6-ACA formed into caprolactam was started by injecting the sample onto a gas chromatograph coupled to a mass spectrometer (GC-MS as described above). By comparing the results with those obtained with injection onto the same gas chromatograph of a chemical blanc solution consisting of potassium phosphate buffer (100 ml, pH 6.0), 20 mM 6-AHEA and 0.23 mM NADH the cyclization of the 6-ACA formed in the biotransformation could be confirmed. The amount of caprolactam so obtained was calculated at about 2.7 ppm.

The invention claimed is:

1. Process for the biochemical synthesis of 6-amino caproic acid wherein either 6-aminohex-2-enoic acid of formula [1](6-AHEA)

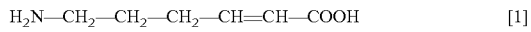  [1]

or wherein 6-amino-2-hydroxy-hexanoic acid (6-AHHA), a compound capable of being transformed into 6-aminohex-2-enoic acid, is treated with an enzyme having α,β-enoate reductase activity towards molecules containing an α,β-enoate group and a primary amino group, in particular with an enzyme having α,β-enoate reductase activity towards 6-aminohex-2-enoic acid in the presence of NADH or NADPH to synthesize 6-amino caproic acid.

2. Process for the biochemical synthesis of 6-amino caproic acid wherein either 6-aminohex-2-enoic acid of formula [1](6-AHEA)

$$H_2N-CH_2-CH_2-CH_2-CH=CH-COOH \quad [1]$$

or 6-amino-2-hydroxy-hexanoic acid (6-AHHA), a compound capable of being transformed into 6-aminohex-2-enoic acid, is treated with an enzyme having α,β-enoate reductase activity towards molecules containing an α,β-enoate group and a primary amino group, characterized in that the enzyme having α,β-enoate reductase activity is an enzyme originating from a microorganism selected from the group consisting of species of *Acetobacterium* sp., *Acremonium* sp., *Agrobacterium* sp., *Burkholderia* sp., *Cephalosporium* sp., *Clostridium* sp., *Escherichia* sp., *Moorella* sp., *Ochrobactrum* sp., *Pseudomonas* sp., *Salmonella* sp., *Shigella* sp., *Tilachildium* sp., *Yersinia* sp., and *Vibrio* sp. in the presence of NADH or NADPH to synthesize 6-amino caproic acid.

3. Process for the biochemical synthesis of 6-amino caproic acid wherein either 6-aminohex-2-enoic acid of formula [1](6-AHEA)

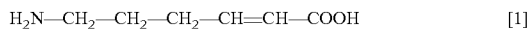

or 6-amino-2-hydroxy-hexanoic acid (6-AHHA), a compound capable of being transformed into 6-aminohex-2-enoic acid, is treated with an enzyme having $\alpha,\beta$-enoate reductase activity towards molecules containing an $\alpha,\beta$-enoate group and a primary amino group, characterized in that the enzyme having $\alpha,\beta$-enoate reductase activity is an enzyme originating from *Acremonium* sp., *Clostridium* sp., *Moorella* sp. or *Ochrobactrum* sp. in the presence of NADH or NADPH to synthesize 6-amino caproic acid.

4. Process according to claim 3, characterized in that the enzyme having $\alpha,\beta$-enoate reductase activity is an enzyme from *Acremonium strictum* CBS114157, *Clostridium tyrobutyricum* DSM1460, *Moorella thermoacetica* DSM1974, *Ochrobactrum anthropi* NCIMB41200, or *Clostridium kluyveri* DSM555.

5. Process for the biochemical synthesis of 6-amino caproic acid wherein either 6-aminohex-2-enoic acid of formula [1](6-AHEA)

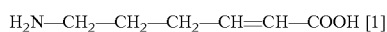

or 6-amino-2-hydroxy-hexanoic acid (6-AHHA), a compound capable of being transformed into 6-aminohex-2-enoic acid, is treated with an enzyme having $\alpha,\beta$-enoate reductase activity towards molecules containing an $\alpha,\beta$-enoate group and a primary amino group, characterized in that the enzyme having $\alpha,\beta$-enoate reductase activity has aerostable $\alpha,\beta$-enoate reductase activity and is an enzyme originating from a microorganism selected from the group consisting of species of *Agrobacterium* sp., *Burkholderia* sp., *Escherichia* sp., *Pseudomonas* sp., *Salmonella* sp., *Shigella* sp., *Yersinia* sp., and *Vibrio* sp. in the presence of NADH or NADPH to synthesize 6-amino caproic acid.

6. Process for the biochemical synthesis of 6-amino caproic acid wherein either 6-aminohex-2-enoic acid of formula [1](6-AHEA)

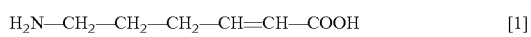

or 6-amino-2-hydroxy-hexanoic acid (6-AHHA), a compound capable of being transformed into 6-aminohex-2-enoic acid, is treated with an enzyme having aerostable $\alpha,\beta$-enoate reductase activity towards molecules containing an $\alpha,\beta$-enoate group and a primary amino group, characterized in that the enzyme having aerostable $\alpha,\beta$-enoate reductase activity is an enzyme originating from an *Escherichia coil* species in the presence of NADH or NADPH to synthesize 6-amino caproic acid.

7. Process according to claim 6, characterized in that the enzyme having aerostable $\alpha,\beta$-enoate reductase activity is an enzyme originating from *Escherichia coil* K12.

8. Process according to claim 1, characterized in that 6-aminohex-2-enoic acid is being converted into 6-amino caproic acid at a pH in the range from 3 to 9.

9. Process according to claim 8, characterized in that the pH is in the range of from 4 to 8.

10. Process according to claim 9, characterized in that the pH is in the range of from 5 to 8.

11. Process according to claim 8, characterized in that the pH is in the range of from 5.5 to 7 under anaerobic conditions or of from 6.5 to 8 under aerobic conditions.

12. Process according to claim 1, characterized in that the process is carried out in a host organism selected from the group consisting of genera of *Aspergillus, Bacillus, Corynebacterium, Escherichia* and *Pichia*.

13. Process according to claim 12, characterized in that the process is carried out in a host organism selected from the group consisting of *Escherichia coil, Corynebacterium glutamicum, Aspergillus niger* and *Pichia pastoris* host organisms.

14. Process according to claim 12, characterized in that in the host organism an $\alpha,\beta$-enoate reductase gene encoding an enzyme having $\alpha,\beta$-enoate reductase activity towards molecules containing an $\alpha,\beta$-enoate group and a primary amino group is cloned and expressed.

15. A process for biochemically synthesizing 6-amino caproic acid, the process comprising treating 6-aminohex-2-enoic acid of formula [1](6-AHEA)

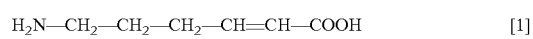

with an enzyme having $\alpha,\beta$-enoate reductase activity towards molecules containing an $\alpha,\beta$-enoate group and a primary amino group in the presence of NADH or NADPH to synthesize 6-amino caproic acid.

16. The process according to claim 15, wherein the enzyme having $\alpha,\beta$-enoate reductase activity is an enzyme originating from a microorganism selected from the group consisting of species of *Acetobacterium* sp., *Acremonium* sp., *Agrobacterium* sp., *Burkholderia* sp., *Cephalosporium* sp., *Clostridium* sp., *Escherichia* sp., *Moorella* sp., *Ochrobactrum* sp., *Pseudomonas* sp., *Salmonella* sp., *Shigella* sp., *Tilachildium* sp., *Yersinia* sp., and *Vibrio* sp.

17. The process according to claim 15, wherein the enzyme having $\alpha,\beta$-enoate reductase activity is an enzyme originating from *Acremonium* sp, *Clostridium* sp., *Moorella* sp., or *Ochrobactrum* sp.

18. The process according to claim 17, wherein the enzyme having $\alpha,\beta$-enoate reductase activity is an enzyme from *Acremonium strictum* CBS 114157, *Clostridium tyrobutyricum* DSM1460, *Moorella thermoacetica* DSM1974, *Ochrobactrum anthropi* NCIMB41200, or *Clostridium kluyveri* DSM555.

19. The process according to claim 15, wherein the enzyme having $\alpha,\beta$-enoate reductase activity has aerostable $\alpha,\beta$-enoate reductase activity and is an enzyme originating from a microorganism selected from the group consisting of species of *Agrobacterium* sp., *Burkholderia* sp., *Escherichia* sp., *Pseudomonas* sp., *Salmonella* sp., *Shigella* sp., *Yersinia* sp., and *Vibrio* sp.

20. The process according to claim 19, wherein the enzyme having aerostable $\alpha,\beta$-enoate reductase activity is an enzyme originating from an *Escherichia coil* species.

21. The process according to claim 15, wherein 6-amino-hex-2- enoic acid is being converted into 6-amino caproic acid at a pH in the range from 3 to 9.

22. The process according to claim 21, wherein the pH is in the range of from 4 to 8.

23. The process according to claim 22, wherein the pH is in the range of from 5 to 8.

24. The process according to claim 21, wherein the pH is in the range of from 5.5 to 7 under anaerobic conditions or of from 6.5 to 8 under aerobic conditions.

25. The process according to claim 15, wherein the process is carried out in a host organism selected from the group consisting of genera of *Aspergillus, Bacillus, Corynebacterium, Escherichia,* and *Pichia*.

26. The process according to claim 25, wherein the process is carried out in a host organism selected from the group consisting of *Escherichia coli, Corynebacterium glutamicum, Aspergillus niger*, and *Pichia pastoris* host organisms.

27. The process according to claim 25, wherein in the host organism an α,β-enoate reductase gene encoding an enzyme having α,β-enoate reductase activity towards molecules containing an α,β-enoate group and a primary amino group is cloned and expressed.

* * * * *